US005651614A

United States Patent [19]
Juneau

[11] Patent Number: 5,651,614
[45] Date of Patent: Jul. 29, 1997

[54] CLOUD POINT AND POUR POINT ANALYZER

[75] Inventor: Randy J. Juneau, The Woodlands, Tex.

[73] Assignee: BetzDearborn Inc., Trevose, Pa.

[21] Appl. No.: 376,316

[22] Filed: Jan. 20, 1995

[51] Int. Cl.$^6$ .......................... G01N 25/02; G01N 25/04
[52] U.S. Cl. .................................. 374/17; 374/23
[58] Field of Search .................... 374/20, 17, 18, 374/19, 22, 23

[56] References Cited

U.S. PATENT DOCUMENTS

| | | | |
|---|---|---|---|
| 3,201,970 | 8/1965 | Beaugh et al. | 374/23 |
| 3,643,492 | 2/1972 | Simpson | 374/23 |
| 4,164,136 | 8/1979 | Wiggins et al. | 374/23 |
| 4,519,717 | 5/1985 | Jones et al. | 374/20 |
| 4,677,567 | 6/1987 | Grosser et al. | 364/502 |
| 4,897,797 | 1/1990 | Free, Jr. | 364/500 |
| 5,088,833 | 2/1992 | Tsang et al. | 374/20 |
| 5,209,566 | 5/1993 | Kuwata | 374/22 |

FOREIGN PATENT DOCUMENTS

| | | | |
|---|---|---|---|
| 0073659 | 5/1982 | Japan | 374/17 |
| 0851351 | 7/1981 | U.S.S.R. | 374/17 |

OTHER PUBLICATIONS

Alcor Pour Point Detector brochure P/N 85351 (No Date).
Cloud Point Monitor, Catalog 42668, Bulletin 42668 AX–12, Precision Scientific, Inc. (No Date).
General Pour Pointer, Catalog 44670, Bulletin 44670 AW–11, Precision Scientific, Inc. (No Date).
1993 Annual Book of ASTM standards, Sec. 5, vol. 5.01 Petroleum Products and Lubricants (I): D2500–91, pp. 883–885 and D 97–87, pp. 57–59 (1993).

"Automatic Measuring Instrument of Cloud Point and Pour Point of Petroleum Product or the Like", Patent Abstract vol. 010, No. 324 (P–512), 5 Nov. 1986, (Patent JP 61132849, published Jun. 20, 1986).
"Photoelectric Type Automatic and Continuous Detection of Process Cloud Point, Low Temperature Filter Clogging Point and Freezing Point", Patent Abstract, vol. 10, No. 382 (P–529), 20 Dec. 1986, (Patent JP 61173140, published Aug. 4, 1986).
Abstract for EP 533562A2 (No Date of Publication).
Abstract for EP 41458A (No Date of Publication).
Abstract for FR 2338488A (No Date of Publication).

*Primary Examiner*—Diego F. F. Gutierrez
*Attorney, Agent, or Firm*—Alexander D. Ricci; Matthew W. Smith

[57] ABSTRACT

An apparatus and a method for automatic determination of cloud point temperature and pour point temperature of a petroleum fraction. The apparatus is comprised of a receptacle for holding a sample of the petroleum fraction, a light source, a light detector, heaters, coolers and a proximity sensor combined with a motion indicator to determine cloud and pour point temperature. The apparatus has thermocouples to determine the temperature of samples within the container as the sample is heated and cooled. Measurements of light refraction are used to determine cloud point temperature. Detection of the freezing in place of a motion indicator is used to determine pour point temperature. The apparatus is particularly useful for determining the cloud point and pour point temperatures of middle distillate petroleum fuels and the pour point temperature of dark oils and for determining the amount of pour point depressant needed to achieve desired cloud and pour point temperatures in a fuel.

2 Claims, 5 Drawing Sheets

CLOUD POINT AND POUR POINT ANALYZER

FIELD OF THE INVENTION

The present invention relates to determination of cloud and pour point temperatures of a hydrocarbon. More particularly, the present invention relates to an apparatus and a method for automatically determining the cloud and pour point temperatures of a petroleum fraction containing dissolved wax.

BACKGROUND OF THE INVENTION

Some petroleum fractions, particularly middle distillate petroleum fuels and dark oils typically contain varying quantities of dissolved wax. Waxes are hydrocarbons of high molecular weight which are solids at about 70° F. or less such as paraffin and microcrystalline. Wax has a tendency to crystallize within a petroleum fraction as the petroleum fraction temperature decreases. Crystallized wax causes the petroleum fraction to cloud, become viscous and, as the temperature drops, to solidify. A particular problem exists during the winter months when wax crystallization caused by low outdoor temperatures can cause fuel lines, filters and the like to clog in diesel engines and furnaces which burn petroleum fractions.

Pour point depressants such as kerosene and polymerized higher esters of acrylic acid derivatives are well known in the art. When added to a petroleum fraction, pour point depressants lower the cloud point and the pour point temperature of the petroleum fraction. Kerosene is also used as a diluent to lower the cloud point of petroleum fractions. However, wax content within a petroleum fraction often varies with the distillation conditions under which the fraction was produced and with the source of crude oil from which the fraction was distilled. Thus, the amount of pour point depressant needed to achieve a desired pour point in a petroleum fraction will vary.

Standard tests have been developed by the American Society for Testing and Materials (ASTM) to determine cloud and pour point temperatures. The cloud point temperature test, ASTM D2300-91, determines the temperature at which a cloud of wax crystals will form in a volume of petroleum product. The pour point temperature test ASTM D97-87 determines the lowest temperature at which a petroleum product will flow. Both ASTM D2500-91 and D97-87 are manual tests which require hands on manipulation of petroleum product samples to determine cloud and pour point temperatures.

To account for weather extremes, it is generally desirable to utilize fuels (petroleum fractions) having pour points at least about 10–15° F. below the anticipated operating temperature of a fuel. To depress the cloud and pour point temperatures of fuels to a desired temperature it is common practice to remove a sample of fuel from a refinery production stream, add a pour point depressant to the fuel sample, conduct ASTM's D97-87 and D2500-91 to determine the pour point depressant's effect on the sample and to repeat these steps until addition of pour point depressant results in desired cloud and pour point temperatures in the sample. A proportional amount of pour point depressant is then injected into the process stream to lower the pour point of the fuel before it is shipped for use. Since ASTM's D97-87 and D2500-91 are manual tests this process is very time consuming.

Attempts have been made to eliminate the manual determination of cloud and pour point temperatures. An apparatus utilizing a microprocessor controlled photocell is available commercially from Precision Scientific, Inc. of Chicago, Ill., which determines the cloud point temperature of a material. A separate apparatus utilizing air pressure pulses to determine pour point temperature is also available commercially from Precision Scientific, Inc. Alcor Engineering manufactures a pour point tester utilizing a weighted ring which is visually monitored for cessation of movement by the tester user to determine the pour point temperature of a material. However, a single unitary apparatus is not currently available to determine both cloud and pour point temperatures of a material.

Therefore, a need exists for an apparatus and a method for using the apparatus to automatically determining cloud and pour point temperatures of petroleum fractions. A need also exists for an apparatus which can be utilized on line with an automatic chemical feed system to depress the cloud and pour point temperatures of petroleum fractions as they are processed.

It is an object of this invention to provide an apparatus and a method of using the apparatus to automatically determine both cloud and pour point temperatures of a petroleum fraction. It is also an object of this invention to provide an apparatus which can be installed on-line with a petroleum fraction production stream to automatically determine cloud and pour point temperatures of a petroleum fraction taken from the production stream. It is yet another object of this invention to provide an apparatus and a method of using the apparatus to automatically depress the cloud and pour point temperatures of a petroleum fraction to temperatures less than or equal to predetermined temperatures.

SUMMARY OF THE INVENTION

To achieve the foregoing and other objects, and in accordance with the present invention, as embodied and broadly described herein, one characterization of the present invention comprises an apparatus for automatic, determination of the cloud point temperature and the pour point temperature of a petroleum fraction. The apparatus is comprised of a receptacle having a chamber for holding a petroleum fraction sample; a light emitting means attached to the receptacle and positioned to emit light into the chamber; a light detecting means attached to the receptacle and positioned to detect light emitted into the chamber by the light emitting means; temperature measuring means attached to the receptacle for measuring the temperature of the sample within the receptacle chamber; heating means in thermal contact with the receptacle; cooling means in thermal contact with the receptacle; motion producing means attached to the receptacle; motion indicating means attached to said motion producing means; a motion detecting means positioned adjacent the motion indicating means and a programmable logic controller in electrical communication with the light detecting means, the temperature measuring means, the heating means, the cooling means, the motion producing means and the motion detecting means. The programmable logic controller controls heating, incremental cooling and testing of the petroleum fraction sample to determine the cloud and pour point temperatures of the petroleum fraction.

The method of the invention comprises incrementally cooling the petroleum fraction sample and emitting light into the sample to determine the cloud point temperature of the sample as indicated by light lost to refraction due to wax crystallization. The pour point temperature of a petroleum fraction sample is determined by incrementally cooling the sample and using a movement indicator and motion detecting means to detect that the sample has solidified.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE PREFERRED EMBODIMENTS

Figure 1:
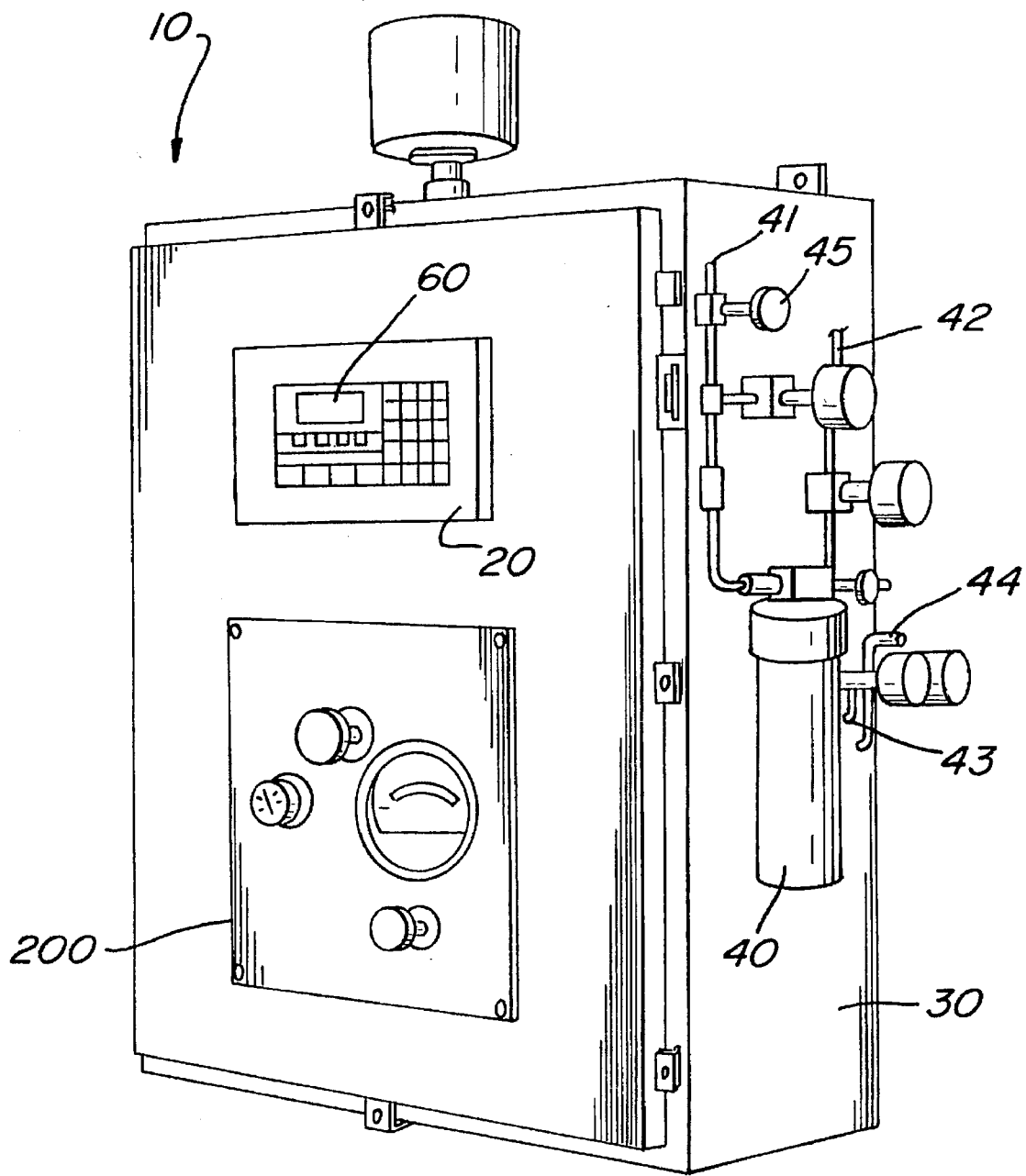
FIG. 1 is a perspective view depicting the cloud point temperature and pour point temperature analyzer apparatus of the present invention.

An automatic cloud point temperature and pour point temperature analyzer apparatus is shown generally as 10 in FIG. 1.

Figure 2:
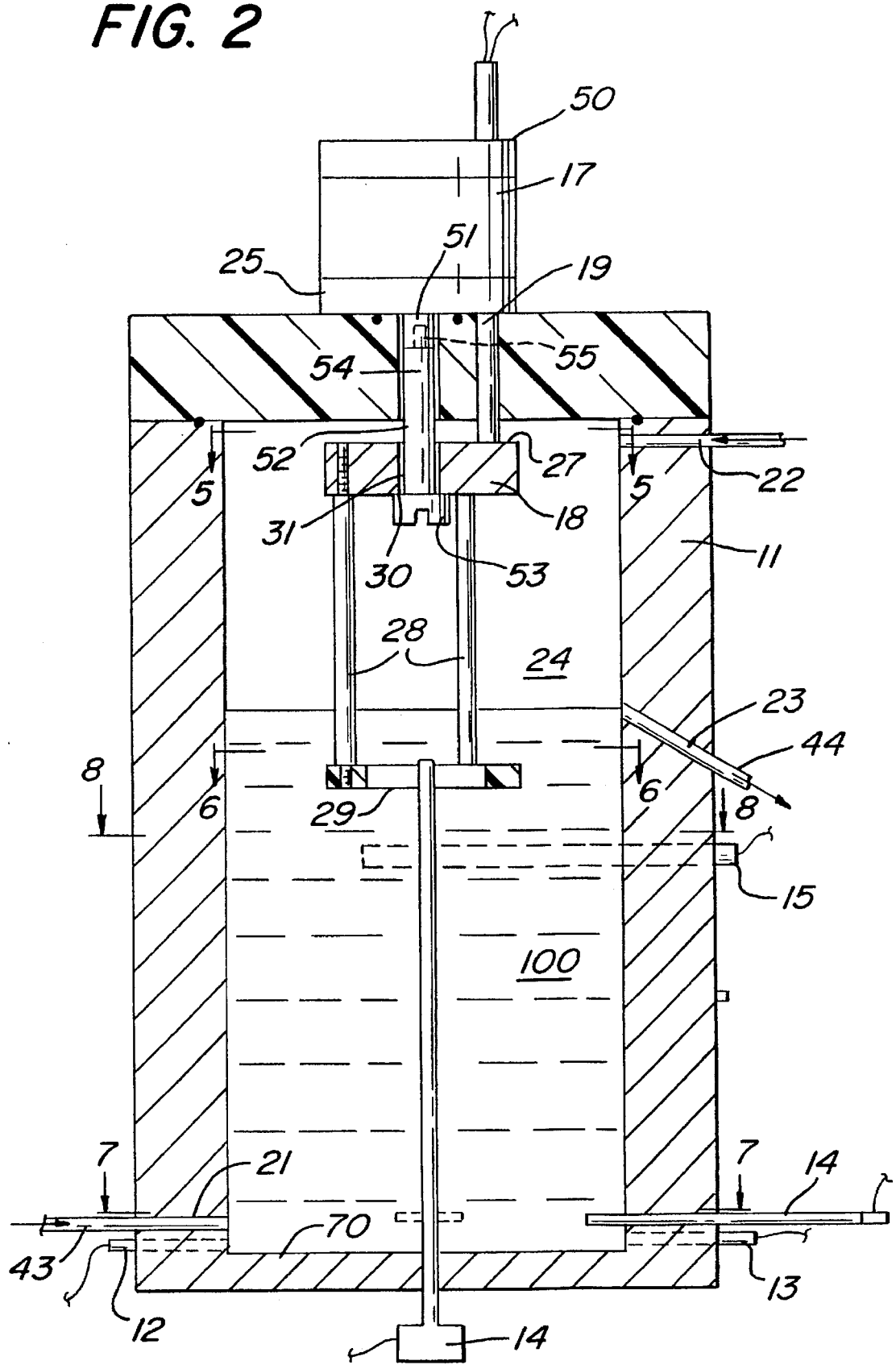
FIG. 2 is a sectional view depicting the receptacle of the present invention.
Figure 7:
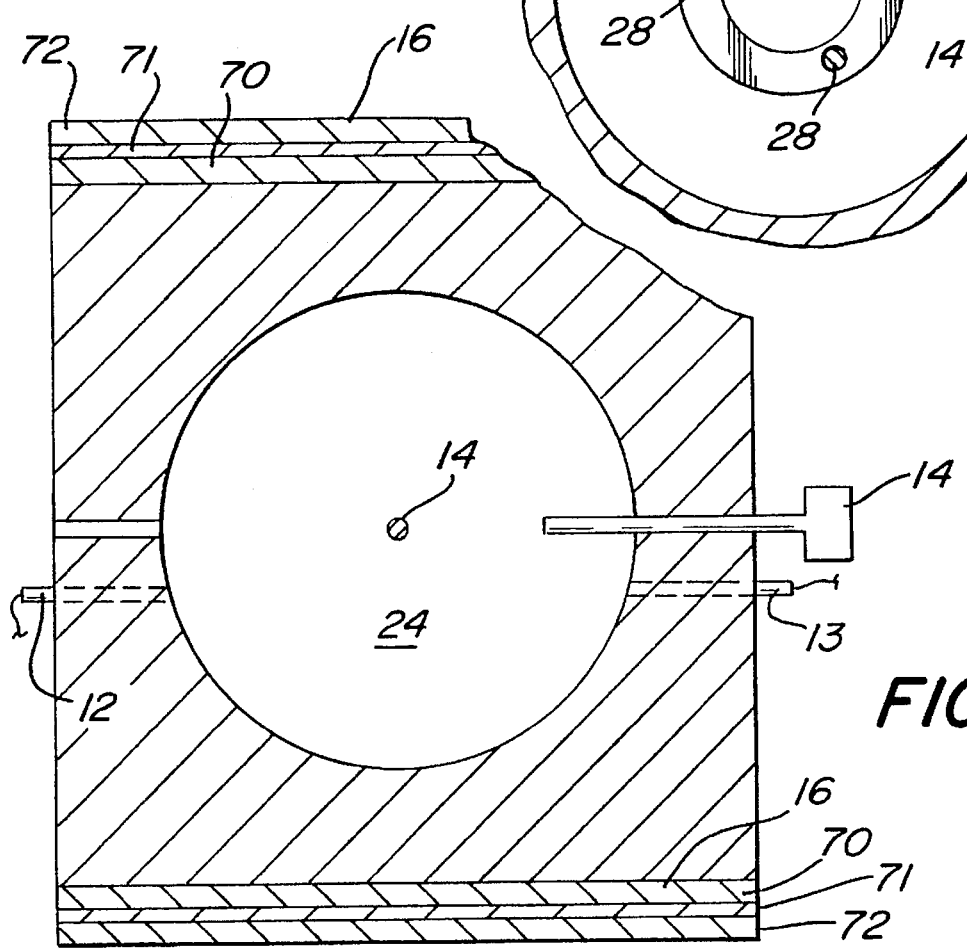
FIG. 7 is a cross-sectional view taken along lines 7—7 of FIG. 2.
Figure 8:
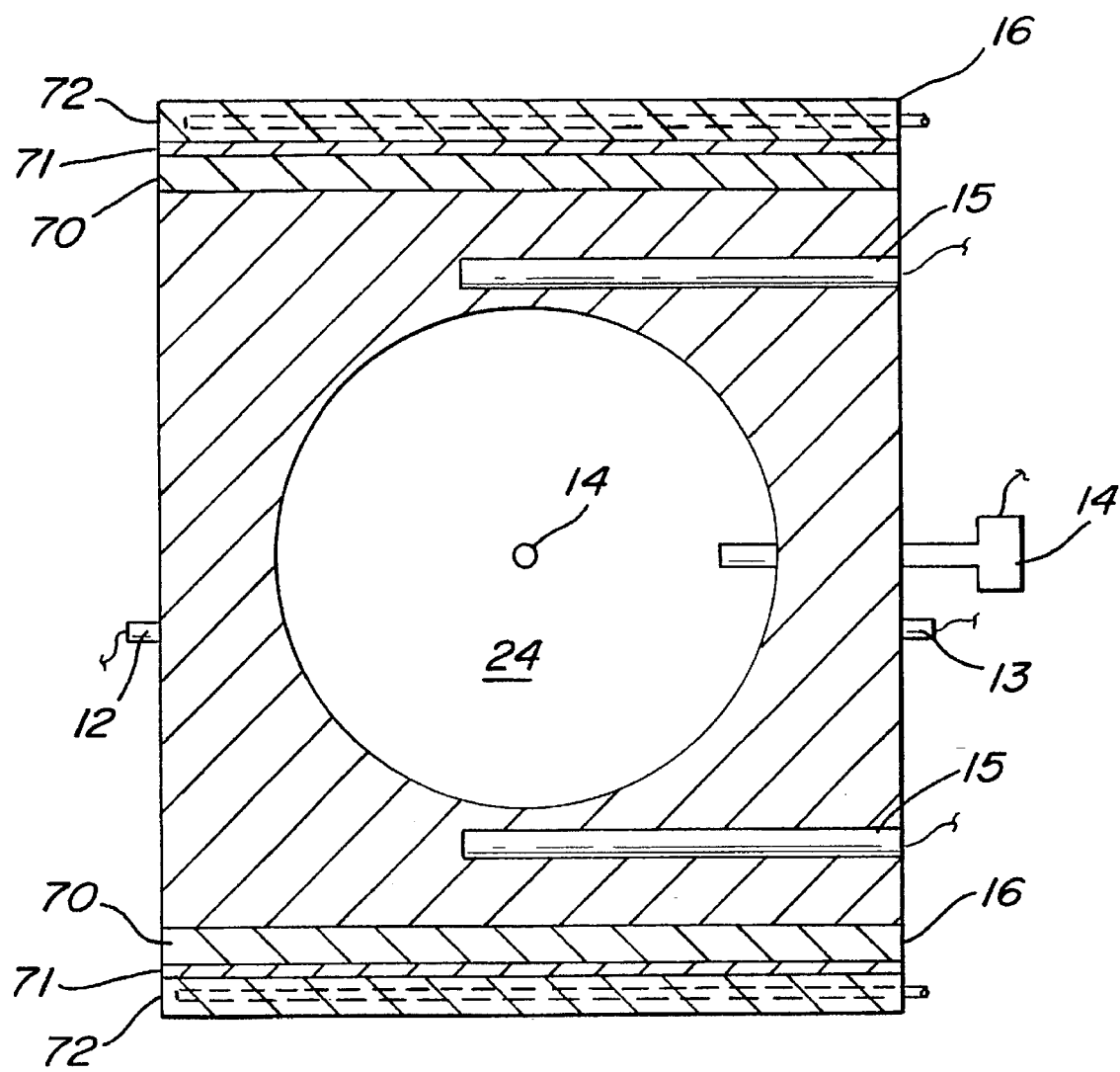
FIG. 8 is a cross-sectional view taken along lines 8—8 of FIG. 2.

The apparatus is comprised of a receptacle 11, a light emitting means 12, a light detecting means 13, temperature measuring means 14, heating means 15, a motion producing means 17, a motion indicating means 18, a motion detecting means 19 as shown in FIG. 2, cooling means 16 shown in FIGS. 7 and 8, and a programmable logic controller 20 shown in FIG. 1.

Receptacle 11 is a vault constructed of thermally conductive material such as aluminum, stainless steel, ceramic or the like, having a sample inlet port 21, a gas purge port 22 and a sample outlet port 23 as shown in FIG. 2.

Light emitting means 12 is preferably an optical fiber light source which emits light into chamber 24 of receptacle 11. Light detecting means 13 detects light within chamber 24 which is emitted from light emitting means 12 and which is transmitted through a petroleum fraction sample 100. Both light emitting means 12 and light detecting means 13 are electrically connected to programmable logic controller 20 which controls when emitting means 12 emits light and electronically records and stores the amount of light detected by detecting means 13. Light emitting and detecting means of this type are available commercially from Omron of Schaumburg, Ill. Programmable logic controllers of this type are available from Texas Instruments/Siemans of Johnson City, Tenn.

Temperature measuring means 14 are preferably a plurality of dual thermocouples as are well known in the art shown in FIGS. 2, 7 and 8, which measure the temperature of sample 100. Temperature measuring means 14 are electronically connected to programmable logic controller 20 which electronically records and stores the temperature of a sample 100.

Heating means 15 am preferably a plurality of heating rods, having a ceramic core wrapped by a heating wire as are well known in the art, positioned as shown in FIGS. 2 and 8. Cooling means 16 are preferably a plurality of liquid cooled, solid state cold plates attached to the sides of receptacle 13 as shown in FIGS. 7 and 8. The cold plates are generally comprised of a front plate 70 in thermal contact with receptacle 11, a thermoelectric module layer 71 and a liquid cooled back plate 72. Cold plates of this type are available commercially from Thermoelectric Cooling American Corp., Chicago, Ill. Both heating means 15 and cooling means 16 are electrically connected to programmable logic controller 20 which controls actuation of the heating and cooling means.

Motion producing means 17 is preferably an air actuated cylinder having a body 50 and a piston 51, such as available from Bimba Manufacturing of Monee, Ill. Shaft 52 has a head portion 53, a mid-portion 54 and an attachment portion 55 attached to piston 51 as shown in FIG. 2. Motion producing means 17 is attachable to a pressurized air source (not shown) which actuates piston 51. Programmable Logic Controller 20 actuates the pressurized air source and thus controls actuation of motion producing means 17.

Figure 6:
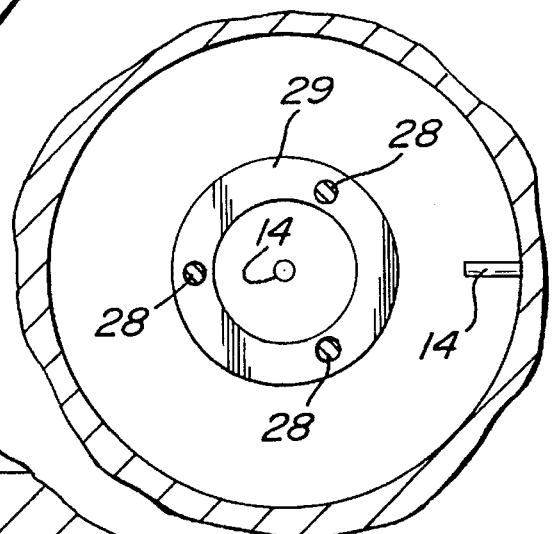
FIG. 6 is a cross-sectional view taken along lines 6—6 of FIG. 2.

Motion indicator means is a means which indicates when a sample of fuel has solidified by ceasing motion. Motion indicator means 18 is preferably comprised of a top member 27, slideably attached to shaft 52 at orifice 31, and attached to a plurality of legs 28 which attach top member 27 to bottom member 29. Bottom member 29 is preferably a flat ring as shown in FIGS. 6.

Motion detecting means 19 is preferably a proximity sensor as is well known in the art which is electronically connected to programmable logic controller 20 which records and stores whether or not top member 27 of motion indicator means 18 is in proximity to motion detecting means 19.

Receptacle 11 is enclosed by a housing 30 as shown in FIG. 1. Housing 30 provides a convenient cabinet for storage, and protection from the environment for the apparatus components. As shown in FIG. 1, housing 30 includes an enclosure protection system 200 which reduces the hazardous area rating within the enclosure to a non-hazardous rating by maintaining positive air pressure within housing 30 to prevent intrusion of explosive vapor into housing 30. Enclosure protection systems are available commercially from Bebco Industries of Texas City, Tex. Hydroscopic dryer 40 is attached to housing 30 and is in fluid communication with a petroleum fraction source (not shown) at inlet 41 and in fluid communication with receptacle 11 at sample inlet duct 43 and sample outlet duct 44. Hydroscopic dryer 40 is preferably a dryer which utilizes a salt such as sodium chloride or potassium chloride to remove trace water from the fuel sample prior to sample cloud and pour point determination. Sample outlet duct 44 is also in fluid communication with the petroleum fraction source (not shown). The petroleum fraction source is preferably a petroleum fraction processing stream.

Apparatus 10 determines cloud point temperature by incrementally cooling a petroleum fraction sample and using light refraction to indicate crystal formation. Pour point temperature is determined by incrementally lowering a samples temperature until a motion indicator becomes frozen within the solidified sample. To utilize apparatus 11 a petroleum fraction sample 100 is removed from a source such as a petroleum fraction processing stream and is injected into inlet 41. Fuel sample 100 is passed through hydroscopic dryer 40 to remove any trace water from the sample which may interfere with cloud point or pour point temperature determination and is injected into receptacle 11 via duct 43 shown in FIG. 1 which is connected to inlet 21 shown in FIG. 2. Sufficient sample 100 is added to chamber 24 of receptacle 11 to submerge bottom member 29 of indicating means 18 as shown in FIG. 2. The cloud and pour point temperatures of sample 100 are determined by:

a) heating sample 100 to at least 115° F. by energizing heating means 15;

b) emitting light into chamber 24 and into sample 100 by energizing light emitting means 12;

c) detecting the light transmitted from emitter 12 through sample 100 by light detecting means 13;

d) cooling sample 100 by deenergizing heating means 15 and activating cooling means 16;

e) emitting light into sample 100 by energizing light emitting means 12;

f) detecting the light transmitted from emitter 12 through sample 100 by light emitting means 13;

g) comparing the amount of light detected in step f) to the amount of light detected in step c) to determine the percent amount of light lost to refraction by wax crystal formation using the equation:

$$\frac{L_c - L_f}{L_c} \times 100 = L_L$$

where:
$L_c$ is the amount of light detected in step c,
$L_f$ is the amount of light detected in step f, and
$L_L$ is the percent amount of light lost to refraction;

h) repeating steps d)–g) until $L_L$ is about 2% or greater;

i) when $L_L$ is about 2% or greater, recording the cloud point temperature of sample 100;

j) cooling sample 100 of step i) by at least 5° F.;

k) moving motion indicating means 18 by actuating motion producing means 17;

l) detecting the movement of motion indicating means 18 by motion detecting means 19;

m) repeating steps j)–l) until no movement of motion indicating means 18 is detected by motion detecting means 19;

n) recording the pour point temperature of sample 100 of step m).

Steps a)–i) are performed by programmable logic controller 20 to automatically determine the cloud point of sample 100 by determining the temperature at which enough wax crystals have formed in sample 100 to cause refraction of at least about 2% of the light emitted into sample 100 by light emitting means 12. Light refraction of 2% generally indicates enough wax crystal formation to be seen by the naked eye therefore indicating cloud point temperature. Programmable logic controller can be adjusted to record a cloud point temperature at varied amounts of light lost to refraction depending on the user's needs.

Figure 3:
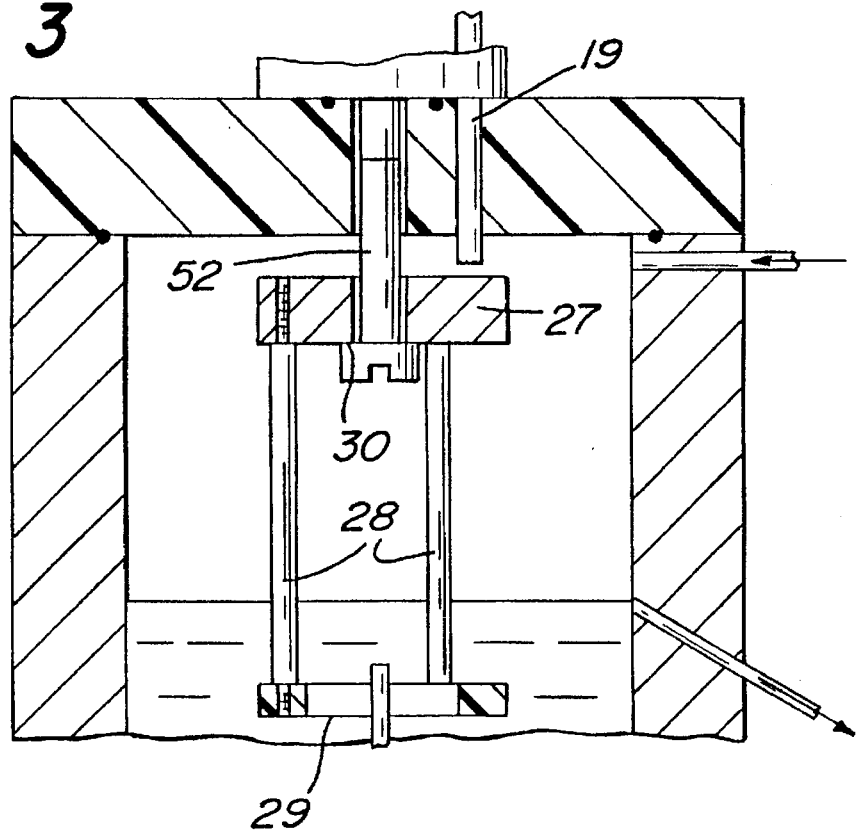
FIG. 3 is a partially cut-away sectional view depicting the motion indicating means.
Figure 4:
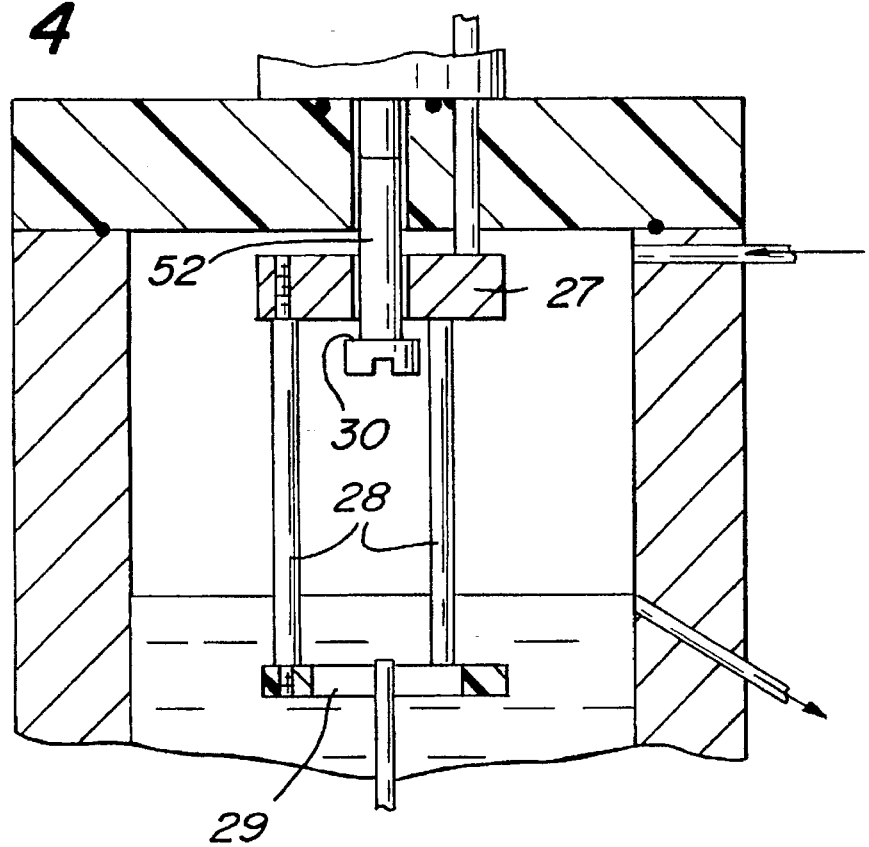
FIG. 4 is a partially cut-away sectional view depicting the motion indicating means.
Figure 5:
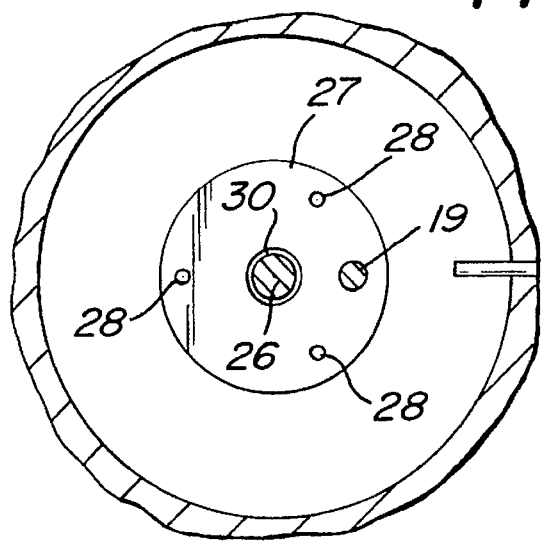
FIG. 5 is a cross-sectional view taken along lines 5—5 of FIG. 2.

Steps j)–n) are performed by programmable logic controller 20 to automatically determine the pour point of sample 100. At temperatures above the pour point of sample 100, in step k), actuation of motion producing means 17 causes shaft 26 to move from the configuration shown in FIG. 2 in which top member 27 rests on shoulder 30 of shaft 52 and in which top member 27 is in proximity of motion detecting means 19, to the configuration shown in FIG. 3 in which top member 27 rests on shoulder 30 of shaft 52 and in which top member 27 is not in proximity of motion detecting means 19. In step l), when motion detecting means 19 detects that top member 27 is no longer in proximity, programmable logic controller 20 repeats steps j)–l). When repeated cooling lowers the temperature of sample 100 to the point where wax crystal formation has solidified sample 100, and after motion producing means 17 moves piston 26 and shaft 52, the solidified sample 100 freezes bottom member 29 in place. Top member 27 is then prevented from movement by legs 28 which are attached to bottom member 29. Top member 27 slides along shaft 52 in orifice 31 of member 27 and remains in proximity of motion sensor 19. This configuration is shown in FIG. 4. When programmable logic controller 20 recognizes that piston 26 has been moved and that top member 27 is still in proximity to motion sensing means 19 the programmable logic controller records that the pour point temperature of the sample has been reached.

The recorded cloud and pour point temperatures are displayed on display panel 60 shown in FIG. 1 which is electrically connected to programmable logic controller 20. Thus, controller 20 automatically heats, incrementally cools and tests sample 100 to determine the cloud point temperature and pour point temperature of sample 100.

ASTM D97-87 requires that the pour point temperature be checked at 5° F. intervals. If the frequency is increased, it is possible to obtain a falsely lower pour point temperature due to disturbance of the wax crystal structure caused by movement of the motion indicator within sample 100.

Solidified sample 100 is removed from chamber 24 by:

o) ceasing cooling with cooling means 16 and energizing heating means 15 until sample 100 is pourable, and p) injecting pressurized gas into chamber 24 through gas purge port 22 and adding fresh fuel into chamber 24 by inlet 21. Steps o) and p) melt and force sample 100 out outlet 23 and out of duct 44 thereby purging the tested sample.

Duct 44 is in fluid communication with the fuel source, thus sample 100 is returned to its source.

If the recorded cloud and pour point temperatures are not low enough for the desired utility of the hydrocarbon, a known amount of cloud and/or pour point depressant can be added to the petroleum fraction source, a fresh sample of depressed petroleum fraction is input into chamber 24 and steps a)–i) are repeated to determine a new cloud point for the depressed sample. Steps a)–i) are repeated until enough cloud point depressant has been added to the petroleum fraction to achieve a desired cloud point temperature. Similarly, a pour point depressant can be added to the petroleum fraction source, a fresh sample of depressed petroleum fraction is added to chamber 24 and steps j)–p) are repeated to determine a new pour point for the depressed sample. Steps j)–p) are repeated until enough pour point depressant has been added to the petroleum fraction to achieve a desired pour point temperature. Controller 20 is preferably utilized with an automatic chemical feed system such as PaceSetter® (U.S. Pat. No. 4,897,797) available commercially from Betz Laboratories, Inc. to automatically add the pour point depressant into the petroleum fraction source.

As an alternative to automatically adding pour point depressant to a petroleum fraction source, small quantities of pour point depressant can be added to a petroleum fraction sample and steps a)–m) repeated after each addition of depressant until the desired cloud and pour point depression has been achieved. A proportional amount of pour point depressant is then added to the petroleum fraction source to achieve the desired cloud and/or pour point temperatures.

If the apparatus is utilized to determine the pour point temperature of a dark oil, steps a)–i) can be skipped and steps j)–p) can be used.

Thus the invention provides an apparatus and a method for utilizing the apparatus to automatically determine the cloud point temperature and pour point temperature of a petroleum fraction. The apparatus and method eliminates time consuming, repetitive manual testing and is particularly useful for on-line determination of cloud and pour point temperatures when the apparatus is in fluid communication with a petroleum fraction production stream. The invention also provides an apparatus and a method of using the apparatus to determine the amount of additives which must be added to a petroleum fraction to depress the cloud and/or pour point temperatures of the fraction to desired temperatures.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

I claim:

1. An apparatus for automatic determination of the cloud point temperature and the pour point temperature of a petroleum fraction, said apparatus comprising:
   a) a receptacle comprising a thermally conductive vault having a chamber for holding a petroleum fraction sample, a sample inlet port, a gas purge port and a liquid outlet port;
   b) a light emitting means attached to said receptacle and positioned to emit light into said chamber, said light emitting means comprising an optical fiber light emitter;
   c) a light detecting means attached to said receptacle and positioned to detect light emitted into said chamber and emitted through said sample by said light emitting means;
   d) a plurality of thermocouples attached to said receptacle for measuring the temperature of said sample inside said chamber of said receptacle;
   e) heating means in thermal contact with said receptacle for heating said receptacle, said heating means comprising a plurality of heating rods;
   f) cooling means in thermal contact with said receptacle for cooling said receptacle, said cooling means comprising a plurality of liquid cooled, solid state cold plates;
   g) motion producing means attached to said receptacle, said motion producing means comprising an air actuated cylinder having a body, a piston attached to said body and a shaft attached to said piston,
   h) a motion indicator means attached to said motion producing means, said motion indicator means comprising a top member slideably attached to said shaft of said motion producing means, a plurality of legs attached to said top member and a bottom member attached to said legs;
   i) a motion detecting means positioned adjacent said motion indicator means, said motion detecting means comprising a proximity sensor for sensing the proximity of said top member of said motion indicating means;
   j) a programmable logic controller in electrical communication with said light emitting, said light detecting, said temperature measuring, said heating, said cooling, said motion detecting and said motion producing means wherein said programmable logic controller controls heating, and incremental cooling of said petroleum fraction sample and whereby the cloud point and pour point temperatures of said petroleum fraction sample are determined;
   k) a housing enclosing said receptacle, light emitting means, light detecting means, plurality of thermocouples, heating means, cooling means, motion producing means, motion indicator means, motion detector means and said controller, said housing including a means for maintaining a positive air pressure within said housing to protect said housing from intrusion of explosive vapors; and
   l) a hydroscopic dryer attached to said receptacle sample inlet port for removing water from petroleum fraction samples, prior to testing said petroleum fraction samples.

2. The apparatus of claim 1 wherein said petroleum fraction sample is a middle distillate fuel or a dark oil.

\* \* \* \* \*